United States Patent
Jan et al.

(10) Patent No.: US 10,524,758 B2
(45) Date of Patent: Jan. 7, 2020

(54) AUTOMATIC EXPOSURE CONTROL SYSTEM FOR A DIGITAL X-RAY IMAGING DEVICE AND METHOD THEREOF

(71) Applicant: Institute of Nuclear Energy Research, Atomic Energy Council, Executive Yuan, R.O.C., Taoyuan (TW)

(72) Inventors: Meei-Ling Jan, Taoyuan (TW); Sheng-Pin Tseng, Taoyuan (TW); Chia-Hao Chang, Taoyuan (TW)

(73) Assignee: INSTITUTE OF NUCLEAR ENERGY RESEARCH, ATOMIC ENERGY COUNCIL, EXECUTIVE YUAN, R.O.C, Taoyuan (TW)

( * ) Notice: Subject to any disclaimer, the term of this patent is extended or adjusted under 35 U.S.C. 154(b) by 346 days.

(21) Appl. No.: 15/596,467

(22) Filed: May 16, 2017

(65) Prior Publication Data

US 2018/0116622 A1 May 3, 2018

(30) Foreign Application Priority Data

Oct. 28, 2016 (TW) .............................. 105135116 A

(51) Int. Cl.
*H05G 1/10* (2006.01)
*G01B 15/02* (2006.01)
(Continued)

(52) U.S. Cl.
CPC .............. *A61B 6/542* (2013.01); *A61B 6/405* (2013.01); *G01B 11/06* (2013.01); *G01B 11/22* (2013.01); *G01B 17/02* (2013.01)

(58) Field of Classification Search
CPC .......... A61B 6/405; A61B 6/542; A61B 6/545; A61B 6/08; A61B 6/0407; A61B 6/544; A61B 5/0022; A61B 5/0075; A61B 5/0077; A61B 5/015; A61B 5/02055; A61B 5/021; A61B 5/02444; A61B 6/469; A61B 5/1077; A61B 5/445; A61B 6/032; A61B 6/0492; A61B 6/06; A61B 6/4447;
(Continued)

(56) References Cited

U.S. PATENT DOCUMENTS 6,233,310 B1 * 5/2001 Relihan .................... H05G 1/46
378/108
6,292,537 B1 * 9/2001 Zimmermann .......... A61B 6/06
378/108
(Continued)

*Primary Examiner* — Irakli Kiknadze
(74) *Attorney, Agent, or Firm* — Locke Lord LLP; Tim Tingkang Xia, Esq.

(57) ABSTRACT

The invention provides an automatic exposure control method for a digital X-ray imaging device. The automatic exposure control method for a digital X-ray imaging device includes the following steps. First, a parameter database is provided before imaging scan. A depth information is generated, wherein the depth information by a depth sensor detect the thickness of a region of interest of an object. Imaging exposure parameters, mAs and kV, are estimated according to the depth information and the parameter database. Then, X-ray imaging is performed according to the imaging exposure parameters estimated by the method described in this application. In addition, an automatic exposure control system for a digital X-ray imaging device is also provided.

8 Claims, 9 Drawing Sheets

(51) Int. Cl.
*H05G 1/64* (2006.01)
*A61B 6/00* (2006.01)
*G01B 11/06* (2006.01)
*G01B 11/22* (2006.01)
*G01B 17/02* (2006.01)

(58) Field of Classification Search
CPC ... A61B 6/4452; A61B 6/4464; A61B 6/4476; A61B 6/583; A61B 6/502; A61B 6/461; A61B 6/586; A61B 2576/00; A61B 5/0059; A61B 5/055; A61B 6/025; A61B 6/0414; A61B 6/107; A61B 6/12; A61B 6/14; A61B 6/4035; A61B 6/4042; A61B 6/482; A61B 6/508; A61B 6/027; A61B 6/0457; A61B 6/4028; A61B 6/4085; A61B 6/4241; G01B 11/06; G01B 11/22; G01B 17/02; G01N 23/04; G01T 1/169; H05G 1/46; H05G 1/58; G21K 1/10

USPC ........................................ 378/95, 98.7, 62, 89

See application file for complete search history.

(56) References Cited

U.S. PATENT DOCUMENTS

| | | | |
|---|---|---|---|
| 6,454,460 B1 * | 9/2002 | Ramanathan | A61B 6/583 |
| | | | 378/158 |
| 9,433,395 B2 * | 9/2016 | Kang | A61B 6/544 |
| 9,904,998 B2 * | 2/2018 | Jockel | A61B 6/08 |
| 2017/0007196 A1 * | 1/2017 | Don | G01B 11/06 |
| 2017/0079610 A1 * | 3/2017 | Morf | A61B 6/542 |
| 2019/0059843 A1 * | 2/2019 | Watanabe | A61B 6/032 |

* cited by examiner

AUTOMATIC EXPOSURE CONTROL SYSTEM FOR A DIGITAL X-RAY IMAGING DEVICE AND METHOD THEREOF

CROSS REFERENCE TO RELATED APPLICATION

This application also claims priority to Taiwan Patent Application No. 105135116 filed in the Taiwan Patent Office on Oct. 28, 2016, the entire content of which is incorporated herein by reference.

FIELD OF THE INVENTION

The present invention relates to an automatic exposure control system and method, and more particularly, to an automatic exposure control system and method for a digital X-ray imaging device.

BACKGROUND OF THE INVENTION

Generally, during an X-ray imaging procedure while an X-ray is projected on a region of interest of a patient, it is inevitable that a radiation risk will be caused as a portion of the radiation dose will deposit in the patient's body when the X-ray is being projected passing through the patient's body toward a digital radiography (DR) device for producing a diagnostic signal or imaging a clinical image. Nevertheless, the dose of radiation that is deposit in the target area and the transmitted intensity of the X-ray can both be affected by the thickness of the patient in the parallel imaging direction, and moreover, the transmitted intensity of the X-ray is further related to the signal-to-noise ratio (SNR) of the image or the optical density (OD) on film. In short, a poor configuration of X-ray imaging parameters that are determined based on patient's body figures can have severe and adverse affect on the resulting image quality as well as the amount of radiation dose being deposited in the target area. As a common knowledge that the size difference between children and adult can be apparent, and that is also true for adult or children of the same age as they can be grown to be fat or skinny. Consequently, individual difference must be considered in the configuration of X-ray imaging parameters, including X-ray voltage (unit: kV), tube current (unit: mA) and exposure time (unit: s). Please refer to FIG. 1, which is a schematic diagram showing imaging results of different X-ray parameter configurations for patients of different body figures. In FIG. 1, the left image is an X-ray image of a patient of 91.2 kg in weight and is obtained by setting the X-ray tube voltage at 114 kV and the product of tube current and exposure time at 3.6 mAs, and the right image is an X-ray image of a patient of 48.9 kg in weight and is obtained by setting the X-ray tube voltage at 92 kV and the product of tube current and exposure time at 2 mAs.

Currently, the X-ray tube voltage, the tube current, and the exposure time are set generally based upon the radiologist's experience according to the patient body figure, the thickness of the target area and pathological features. That is, the two most importance parameters in X-ray imaging are determined solely by experience. However, following the advances in digital radiography, the detective quantum efficiency (DQE) of the current digital radiography device is enhanced and consequently the detective efficiency of the X-ray imaging system using the digital radiography device is enhanced as well. Thereby, a radiologist operating the X-ray imaging system can achieve an image of satisfactory quality using a comparative lower radiation dose than before and thus the risk of cancer from radiation exposure is reduced.

However, clinically radiologists still configure the X-ray tube voltage, the tube current, and the exposure time solely based upon their personal experiences according to the patient body figure and the thickness of the target area, which are achieved via operating a conventional automatic exposure control (AEC) device for controlling the radiation dose without considering the possible affection on image quality coming from the use of a current high performance digital radiography (DR) device. Therefore, even when a DR device of high DQE is available to radiologists, the possibility of taking high quality X-ray images using lower radiation doses is never being considered.

On the other hand, considering the diversity and complexity in the modern DR devices both technologically and materially, the whole parameter configuration process can be very time consuming and labor intensive as operators not only have to be familiar with the DQE performance of the imaging system, but also have to perform individual evaluation process for every patient so as to obtain an optimal imaging parameter for each individual patient. Thus, it is almost impossible for such process to be executed in the real-world hospitals as all real-world hospitals are constantly subjected to the heavy pressure of large amount of imaging workload waiting to be processed. In reality, many modern DR devices had been designed with a pre-scan function for reducing the dependence of the imaging process on the radiologist's experience in view of setting up optimal tube voltage and the product of tube current and exposure time. Although this method is more objective, but it can still be troubled by the shortcoming of excess radiation dose.

Please refer to FIG. 2, which is a schematic diagram showing an automatic expose control (AEC) unit for a conventional DR device. As shown in FIG. 2, the AEC unit is equipped with one or multiple radiation dosimeters, whereas on the upper left shows an AEC chamber 52 with five channels and on the upper right shows AEC chambers 54 of three channels. Operationally, the radiologist on duty will select the proper AEC channels according to the target region of each patient. Thus, the lower left image A1 shows a chest X-ray imaging of correct configuration, while the lower right image A2 shows another chest X-ray imaging of incorrect configuration where the image is overexposed. It is noted that the accessibility and availability of target region can be restricted by the position of AEC channels and the amount thereof as well.

SUMMARY OF THE INVENTION

The primary object of the present invention is to provide an automatic exposure control system for a digital X-ray imaging device that can be used for providing optimized personal X-ray imaging parameter advice to patients in view of minimizing radiation exposure while generating X-ray images with good image quality, so that the risk of cancer can be reduced.

The present invention provides an automatic exposure control method for a digital X-ray imaging device, which can be preformed without any pre-scan process and thus the patient using the method is not subjected to overdosed radiation while at the same time an optimized personal X-ray imaging parameter advice can be provided to the patient, and thereby, not only the patient can have a low-radiation high-quality X-ray imaging, but also the risk of cancer can be reduced.

In an embodiment, the present invention provides an automatic exposure control system for digital X-ray imaging device, which is used for imaging a target object and is comprised of: an X-ray source, a X-ray source controller, a digital X-ray imaging device, a processor, and a depth sensor. The X-ray source controller is used for controlling a tube voltage, a tube current, and a exposure time. The processor has a parameter database and is connected to the X-ray source controller, the digital imaging device, and the depth sensor. The depth sensor is used for detecting a region of interest of the target object so as to obtain a depth information to be transmitted to the processor. After receiving the depth information, the processor performs an estimation process according to the depth information and the parameter database so as to obtain an imaging exposure parameter for the X-ray source controller. After receiving the imaging exposure parameter, the X-ray source controller is enabled to generate an X-ray accordingly to be projected onto the target object, and then to be detected by the digital X-ray imaging device.

The present invention provides an automatic exposure control method for a digital X-ray imaging device. The automatic exposure control method for a digital X-ray imaging device includes the following the steps. First, a parameter database is provided before imaging scan. A depth information is generated, wherein the depth information by a depth sensor detect the thickness of a region of interest of an object. Imaging exposure parameters, mAs and kV values, are estimated according to the depth information and the parameter database. Then, X-ray imaging is performed according to the imaging exposure parameters estimated by the method described in this application.

In addition, the aforesaid automatic exposure control system and method are adapted for a digital X-ray imaging device, and are being designed to use a depth sensor to detect the thickness of a region of interest (e.g. chest) of a target object (e.g. human body) so as to obtain a depth information accordingly, and then imaging exposure parameters can be estimated and obtained by comparing the depth information with a pre-established parameter database. Thereby, an X-ray imaging process can be performed according to the imaging exposure parameters for projecting an X-ray to the target object so as to be detected by the digital X-ray imaging device.

Moreover, the aforesaid automatic exposure control system and method can be performed without the help of an additional single-channel or multi-channel AEC units, and thus, operators are able to select any position on a target object as region of interest without any consideration relating to where the AEC channels, or the availability and amount of ACE channels.

Furthermore, as the aforesaid automatic exposure control system and method can be performed without the need of any pre-scan process, patients will not be subjected to overdosed radiation while at the same time an optimized personal X-ray imaging parameter advice can be provided to the patient, and thereby, not only the patient can have a low-radiation high-quality X-ray imaging, but also the risk of cancer can be reduced.

Further scope of applicability of the present application will become more apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The present invention will become more fully understood from the detailed description given herein below and the accompanying drawings which are given by way of illustration only, and thus are not limitative of the present invention and wherein.

DESCRIPTION OF THE EXEMPLARY EMBODIMENTS

For your esteemed members of reviewing committee to further understand and recognize the fulfilled functions and structural characteristics of the invention, several exemplary embodiments cooperating with detailed description are presented as the follows.

Figure 1:
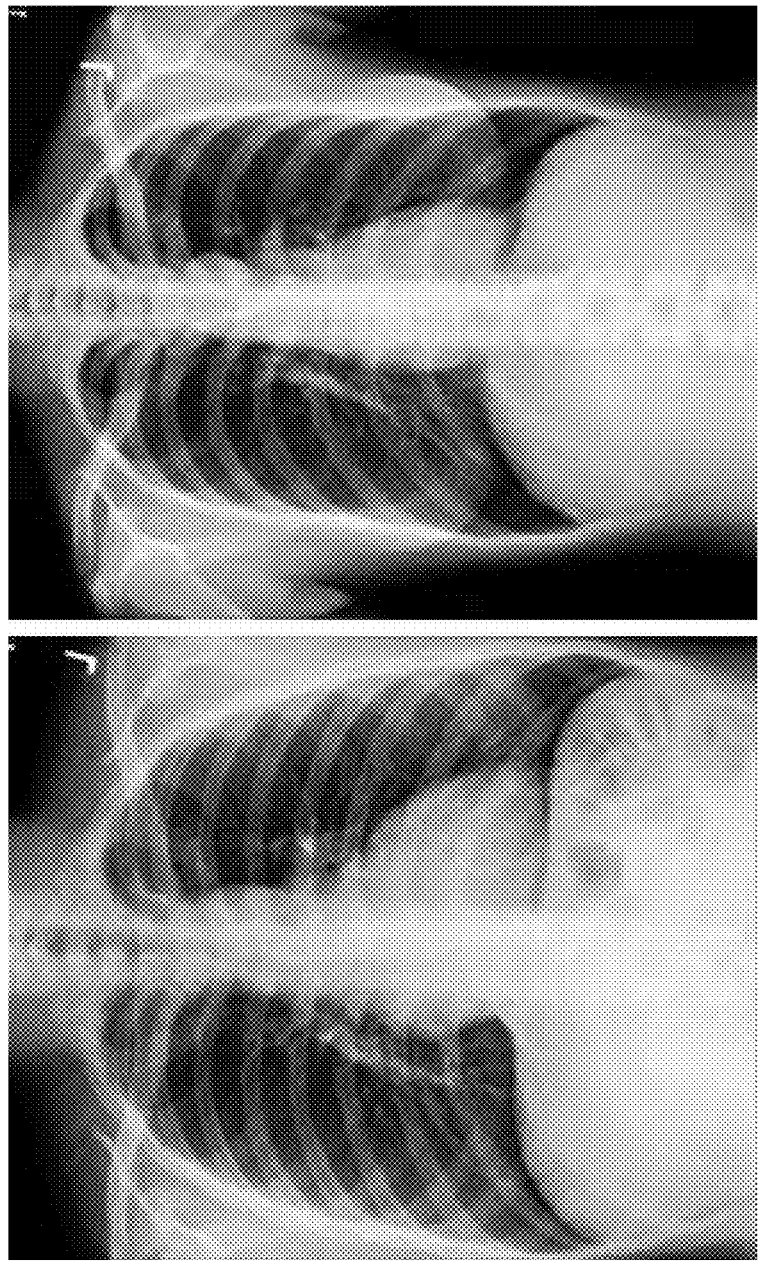
FIG. 1 is a schematic diagram showing imaging results of different X-ray parameter configurations for patients of different body figures.
Figure 2:
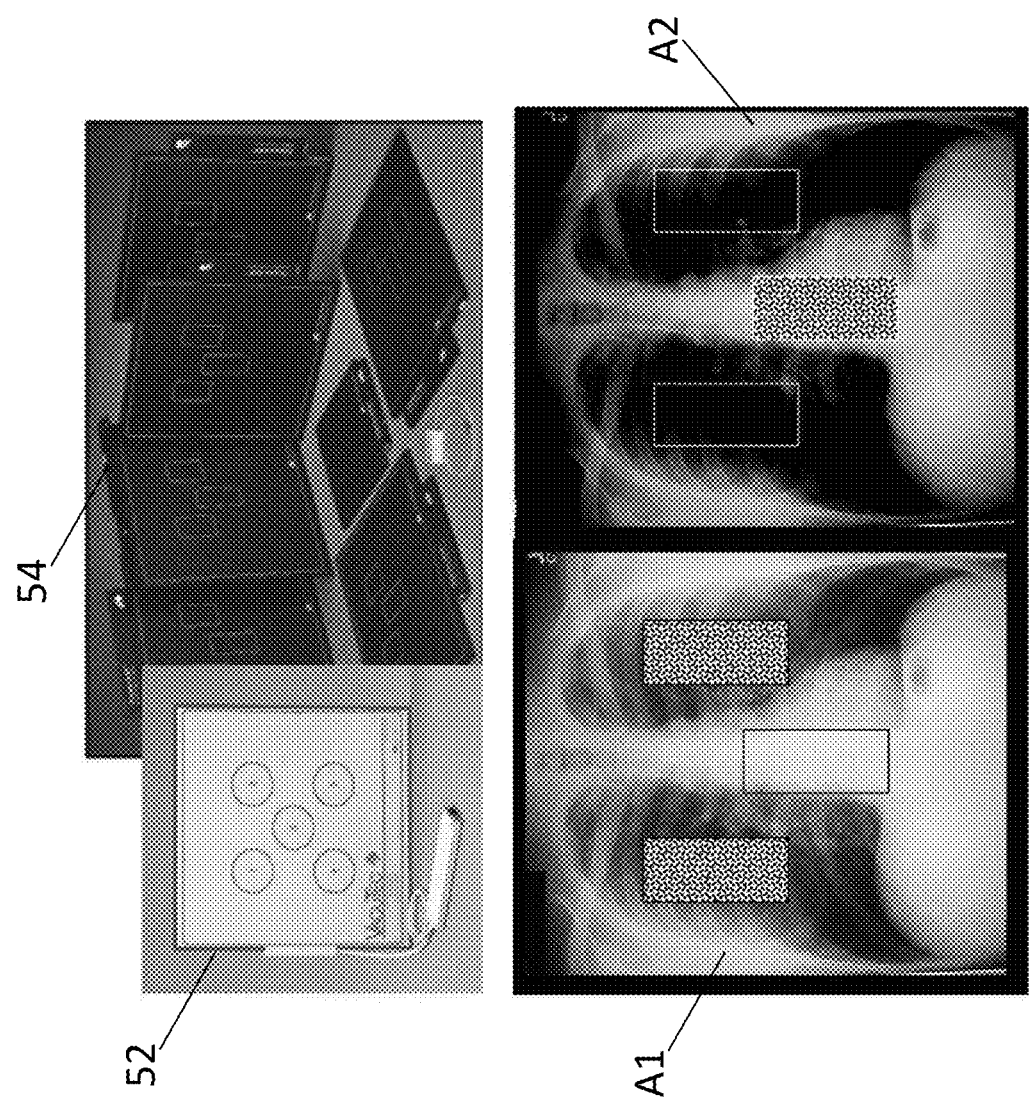
FIG. 2 is a schematic diagram showing an automatic exposure control (AEC) unit for a conventional DR device.
Figure 3:
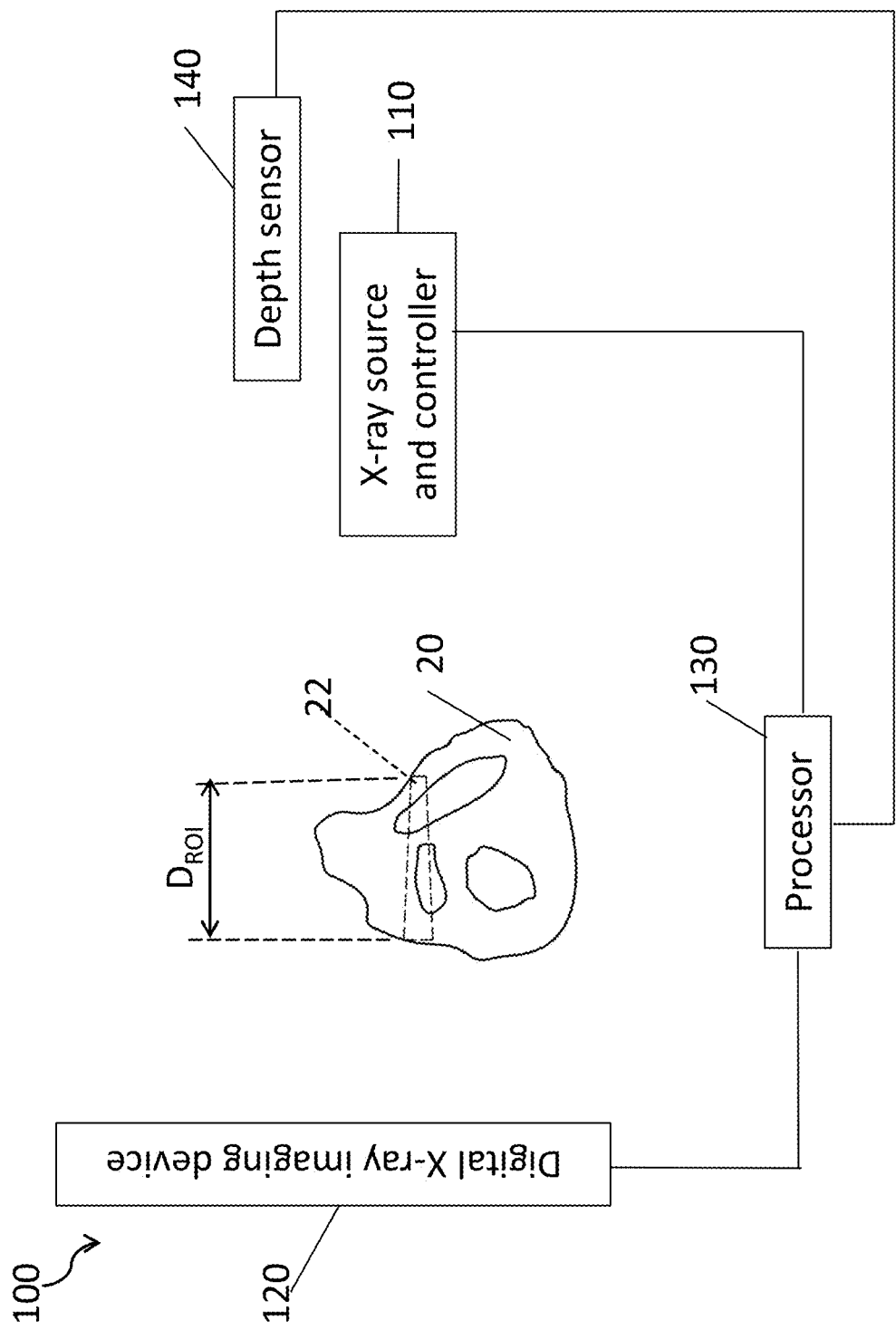
FIG. 3 is a schematic diagram showing an automatic exposure control system according to an embodiment of the present invention.

FIG. 3 is a schematic diagram showing an automatic exposure control system according to an embodiment of the present invention. In FIG. 3, an automatic exposure control system 100 that is adapted for a digital X-ray imaging device is disclosed, which is used for imaging a target object 20, such as a human body. The aforesaid digital X-ray imaging device 120 can be a 2D imaging device or a 3D imaging device, such as a digital radiography (DR) device, a digital tomosynthesis device, or a computed tomography (CT) device, etc., but it is not limited thereby. In addition, the automatic exposure control system 100 comprises an X-ray source, and an X-ray source controller 110, a digital X-ray imaging device 120, a processor 130 and a depth sensor 140.

The X-ray source controller 110 is used for controlling the tube voltage and the product of tube current and exposure time of an X-ray that is emitted out of the X-ray source. In an embodiment of the invention, a collimator is provided for limiting the projection area of the X-ray that is emitted out of the X-ray source inside a specific area for performing a specific imaging operation.

The digital X-ray imaging device 120 is positioned at a specific distance away from the X-ray source and the X-ray source controller 110. However, the aforesaid distance can be adjusted according to actual requirement at will. It is noted that there can be a variety of materials as well as sensing mechanisms capable of being adapted for the digital X-ray imaging device 120 of the invention. For instance, the scintillating materials that can be used in the digital X-ray imaging device 120 can include GOS, CsI(TI), CsI(Na), and so on, and the sensing mechanisms that are used can be TFT, CMOS, CCD, etc., whereas in some cases, a direct-sensing semiconductor, such as a-Se, can be used.

In an embodiment, a lead made grid unit can be arranged at a position between the digital X-ray imaging device 120 and the target object 20, while enabling the grid unit to engage to the surface of the digital X-ray imaging device 120, by that the scattering of the X-ray after passing through the target object 20 is reduced so as to improved the resulting imaging quality.

The processor 130 that is embedded with a parameter database is connected to the X-ray source controller 110, the digital imaging device 120, and the depth sensor 140.

In this embodiment, the depth sensor 140 can be a depth camera, a laser distance sensor, or an ultrasonic distance sensor. It is noted that the depth sensor of the present invention can be any device only if it is a device capable of measuring distance.

Figure 4:
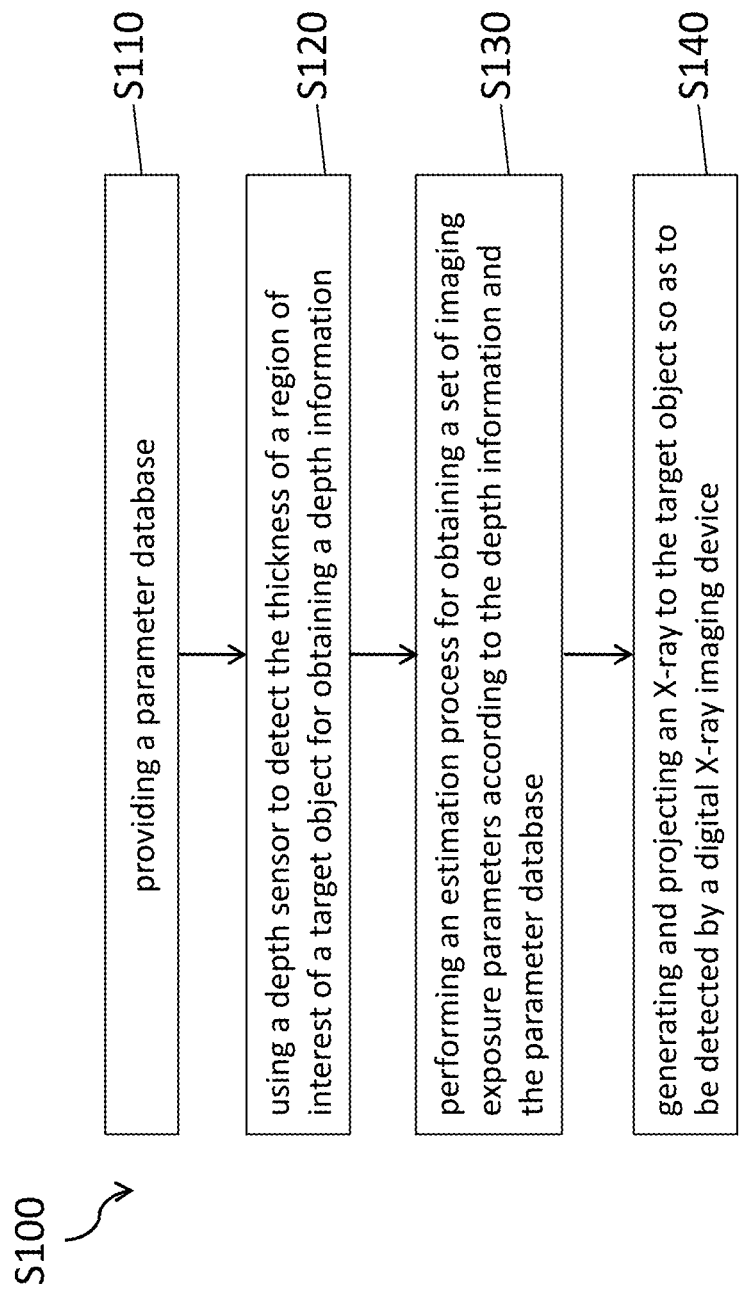
FIG. 4 is a flow chart depicting steps performed in an automatic exposure control method of the present invention.

FIG. 4 is a flow chart depicting steps performed in an automatic exposure control method of the present invention. The steps depicted in the flow chart shown in FIG. 4 are enabled using the automatic exposure control system of FIG. 3.

In this embodiment, the automatic exposure control method S100 is performed for imaging a target object 20, and comprises the steps of: S110~S140.

At step S110, a parameter database is provided. With reference to FIG. 3, a parameter database for a reference object should be established before any imaging, that can be achieved by, first, calibrating the digital imaging device 120 (e.g. either by taking a geometric calibration process, or an uniform calibration process), and enabling the digital imaging device 120 to perform a number of imaging processes with various setting of different tube voltages and the product of tube current and exposure time on each and every region of interest (ROI) 22 of the target object 20, such as chest and head, whereas the imaging processes can be either be enabled on a phantom measurement or by a Monte Carlo digital phantom simulation.

Figure 5:
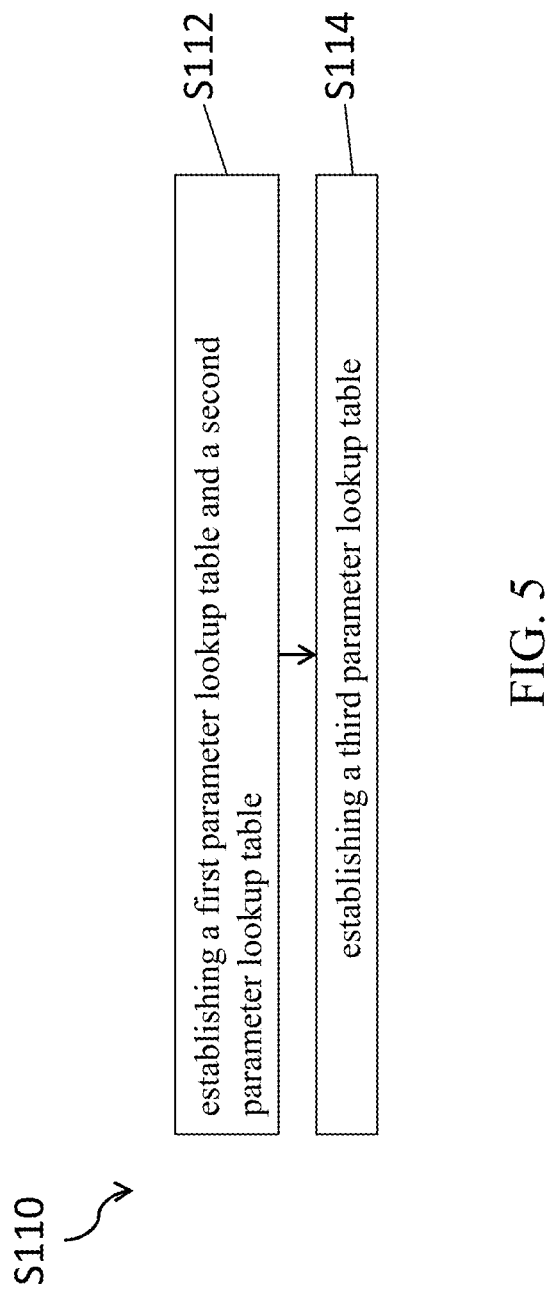
FIG. 5 is a flow chart depicting steps performed in the providing of parameter database that is included in the flow chart of FIG. 4.

FIG. 5 is a flow chart depicting steps performed in the providing of parameter database that is included in the flow chart of FIG. 4. In FIG. 5, the flow starts at the step S112, in which a first parameter lookup table and a second parameter lookup table are established.

Figure 6:
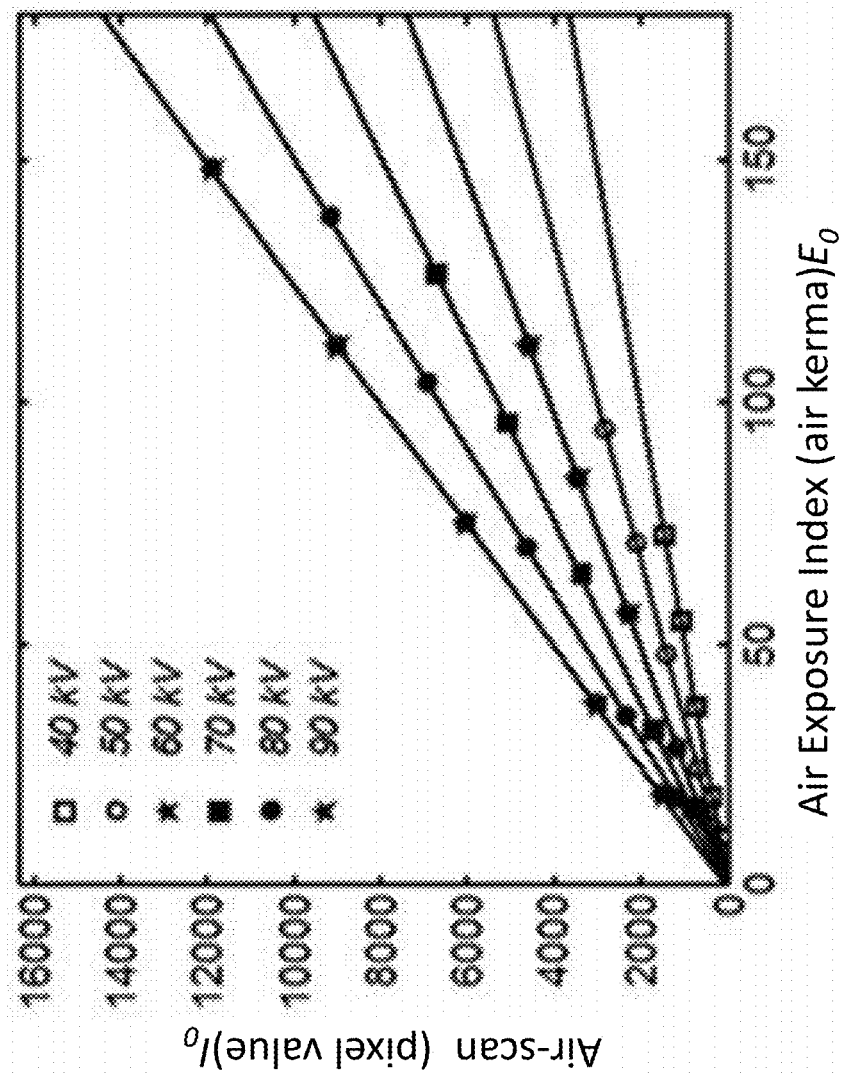
FIG. 6 is a schematic diagram showing the relationship between an air-scan pixel value $I_o$ and an exposure index of air kerma $E_o$.

The first parameter lookup table is established without the target object and at various tube voltages, and is comprised of at least one air-scan pixel value $I_o$ and at least one exposure index of air kerma $E_o$. Please refer to FIG. 6, which is a schematic diagram showing the relationship between an air-scan pixel value $I_o$ and an exposure index of air kerma $E_o$. In FIG. 6, for a specific kV, each air-scan pixel value is linear proportional to each exposure index of air kerma. In another word, the larger that the air-scan pixel value $I_o$ is, the larger the corresponding index of air kerma $E_o$ will be.

The second parameter lookup table includes at least one equivalent thickness $H_{REF}$ relating to the region of interest of a reference object. It is noted that the equivalent thickness $H_{REF}$ can be varied with the projected X-ray energy and the material composition of the target object. It is noted that the difference in the material composition of the target object can generally be presented using mass attenuation coefficient of X-ray in view of unit density $\mu/\rho$, whereas it can be obtained from the mass attenuation coefficient database of the National Institute of Standard and Technology (NIST). After an X-ray is projected entering into a target object, it is affected by the $\mu/\rho$ and the thickness of the target object and thus the number of X-ray photons that travel penetrating the target object is deceased as indicated by the following formula:

$$N = \int_0^{En_{max}} N_0(En) \cdot e^{-\left(\frac{\mu(En)}{\rho}\right) \cdot \rho \cdot \Delta d} dEn;$$

whereas, $N_0$ is the total amount of X-ray photons that is projected entering into a target object;
N is the number of X-ray photons that travel penetrating the target object;
En is the X-ray photon energy;
$\Delta d$ is the thickness of the target object; and
$En_{max}$ is related to the setting of the tube voltage.

In an embodiment when the target object is composed of heterogeneous materials and the total thickness of the heterogeneous target object for the X-ray to penetrate is $$d = \sum_i \Delta d,$$

the equivalent thickness $H_{REF}$ of a reference object can be represent as following:

$$H_{REF}(En) = \sum_i (\mu(En)/\rho)_i \cdot \rho_i \cdot \Delta d / \mu_{REF}(En);$$

whereas, $\mu_{REF}(En)$ is the attenuation coefficient at X-ray energy En for a reference object, such as water.

In addition, the second parameter lookup table is established under various tube voltages with reference to different $(\mu/\rho)$, and geometrical distribution of difference parts of the reference object.

Thereafter, the step S114 is enabled for establishing a third parameter lookup table, whereas the third parameter lookup table includes at least one exposure index $E_{REF}$ relating to the region of interest of the reference object, and at least one pixel value $I_{REF}$ of the digital X-ray imaging device. Referring to the recommendation of AAPM-116, a reference database can be established either by phantom measurement or by Monte Carlo digital phantom simulation at different tube voltages, different body parts κ of a reference object, and different views ν. In the established third parameter lookup table, the $I_{REF}(\kappa,\nu)$ and its corresponding $E_{REF}(\kappa,\nu)$ at different tube voltages are provided. In this embodiment, for a specific tube voltage, each exposure index relating to the region of interest of the reference object $E_{REF}(\kappa,\nu)$ is linear proportional to each pixel value of the digital X-ray imaging device $I_{REF}(\kappa,\nu)$. In another word, the larger that $E_{REF}(\kappa,\nu)$ is, the larger the corresponding $I_{REF}(\kappa,\nu)$ will be.

After the aforesaid parameter databases are established, the step S120 of FIG. 4 can be proceeded, in which a depth sensor 140 is enabled to detect a ROI 22 of the target object 20 so as to obtain a thickness information $H_{ROI}$.

It is noted that the thickness information $H_{ROI}$ that is obtained from the detection of the depth sensor 140 is substantially an equivalent thickness of an actual thickness $D_{ROI}$ measured from the ROI 22 of the target object 20. Operationally, the an actual thickness $D_{ROI}$ can first be obtained by the measurement of the depth sensor 140, and then the depth sensor 140 is enabled to performed a calculation to obtained the equivalent thickness $H_{ROI}$ using the following equation:

$$H_{ROI} = H_{REF} \cdot D_{ROI} / D_{REF},$$

whereas, $D_{REF}$ is the actual thickness of the ROI 22 of a reference object;

$H_{REF}$ is the equivalent thickness of the $D_{REF}$.

In another word, when the reference point remains unchanged, the $H_{ROI}$ value will change with the size change of the target object 20 and the difference in the position of different ROI 22 in the target object 20.

Thereafter, the step S130 is enabled, in which an estimation process is performed for obtaining a set of imaging exposure parameters according to the depth information $H_{ROI}$, and the parameter database, i.e. a tube voltage and a product of tube current and exposure time are obtained.

As shown in FIG. 4, the depth information $D_{ROI}$ from the depth sensor 140 is transmitted to the processor 140, and then the processor 140 first uses the $D_{ROI}$ in a calculation for obtaining $H_{ROI}$ and then enables an estimation process for obtaining a set of imaging exposure parameters by comparing the depth information $H_{ROI}$ to the parameter database.

Figure 7:
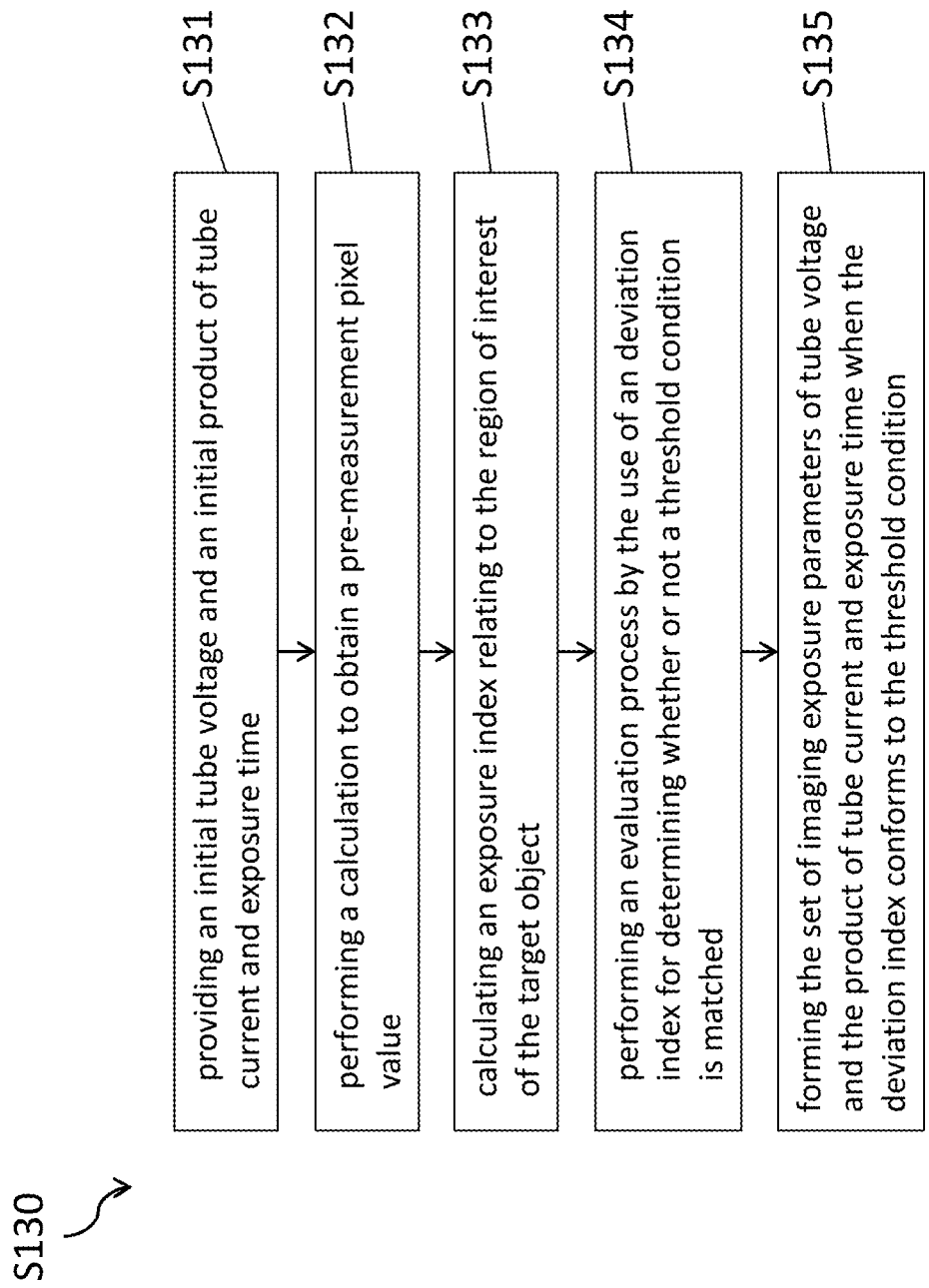
FIG. 7 is a flow chart depicting steps performed in the obtaining of imaging exposure parameters that is included in the flow chart of FIG. 4.

FIG. 7 is a flow chart depicting steps performed in the obtaining of imaging exposure parameters that is included in the flow chart of FIG. 4.

In FIG. 7, the flow starts at the step S131, in which an initial tube voltage and an initial product of tube current and exposure time are provided, whereas the initial tube voltage and the initial product of tube current and exposure time can be obtained by referencing to a tube voltage and a product of tube current and exposure time of a corresponding ROI in a reference object in a manner that: $kV=kV_{REF}$, and $mAs=mAs_{REF}$, but it is not limited thereby. According to the tube voltage and the product of tube current and exposure time with reference to the first parameter lookup table, the corresponding air-scan pixel value $I_o$ and exposure index of air kerma $E_o$ can be obtained.

Thereafter, the step S132 is enabled, in which a pre-measurement pixel value Im is calculated basing upon the air-scan pixel value $I_o$, the X-ray attenuation coefficient $\mu_{REF}$ of a selected reference object, such as water, and the equivalent thickness $H_{ROI}$ relating to the region of interest of the target object, and the pre-measurement pixel value Im is calculated using the following formula:

$$I_m(k,v)=I_0(k,v)e^{-\mu_{REF}H_{ROI}(k,v)},$$

whereas, κ is a specific body part, e.g. a ROI 22 in the target object of the present invention, v represent view, mAs represents the product of tube current and exposure time, while mA is tube current and s is exposure time.

Then, the step S133 is proceeded, in which an exposure index Em relating to the region of interest of the target object is calculated basing upon the exposure index $E_{REF}$ relating to the region of interest of a reference object, the pre-measurement pixel value Im and the pixel value $I_{REF}$ relating to the region of interest of the reference object, while the exposure index $E_m$ relating to the region of interest of the target object can be obtained using the following equation:

$$E_m(k,v)=E_{REF}(k,v) \times I_m(k,v)/I_{REF}(k,v),$$

whereas, $E_{REF}$ and $I_{REF}$ can be obtained with reference to the third parameter lookup table.

At step S134, an evaluation process is performed by the use of a deviation index (DI) for determining whether or not a threshold condition is matched, while allowing the deviation index to be obtained basing upon the difference or ratio between exposure index Em relating to the region of interest of the target object and the corresponding exposure index $E_{REF}$ relating to the region of interest of the reference object. In this embodiment, the DI can be obtained using the following equation:

$$DI=10 \times \log_{10}(E_m(k,v)/E_{REF}(k,v)).$$

At step S135, a set of imaging exposure parameters of tube voltage and the product of tube current and exposure time can be formed when the deviation index conforms to the threshold condition.

Figure 8:
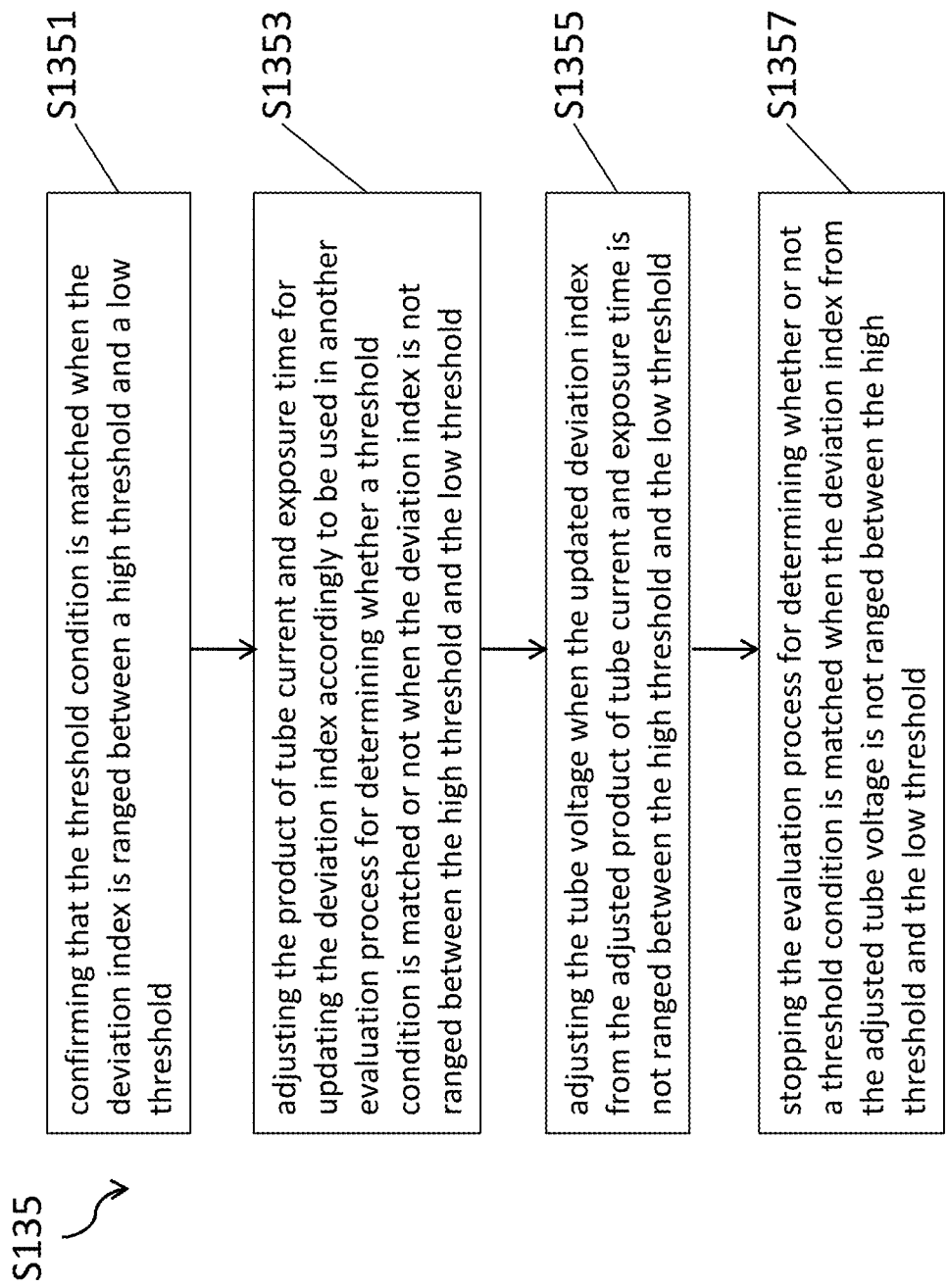
FIG. 8 is a flow chart depicting steps performed in an evaluation process for determining whether or not a threshold condition is matched that is included in the flow chart of FIG. 7.

FIG. 8 is a flow chart depicting steps performed in an evaluation process for determining whether or not a threshold condition is matched that is included in the flow chart of FIG. 7. In FIG. 8, the flow starts at the step S1351. At the step S1351, the threshold condition is confirmed that it had been matched when the deviation index is ranged between a high threshold $\delta_{high}$ and a low threshold and thus the evaluation process is stopped while enabling the step S131 to be proceeded for outputting the corresponding tube voltage and the product of tube current and exposure time to be used as the imaging exposure parameters.

In an embodiment whereas the high threshold $\delta_{high}$ is set to be +0.1, and the low threshold $\delta_{low}$ is set to be −0.1, accordingly the evaluation process for determining whether or not a threshold condition is matched by the use of a deviation index (DI) is stopped when the ratio between Em and $E_{REF}$ is ranged between 0.977 and 1.023, and thus the step S131 is proceeded for outputting the corresponding tube voltage and the product of tube current and exposure time to be used as the imaging exposure parameters. It is noted that there is no restriction to the high threshold $\delta_{high}$ and the low threshold $\delta_{low}$ in the present invention, and thus they can be adjusted at will according to actual requirement.

At step S1353, the product of tube current and exposure time is adjusted for updating the deviation index accordingly to be used in another evaluation process for determining whether a threshold condition is matched or not when the deviation index is not ranged between the high threshold $\delta_{high}$ and the low threshold $\delta_{low}$.

That is, the adjustment to the product of tube current and exposure time is performed in a manner that the product of tube current and exposure time is decreased when the updated deviation index is a positive value, otherwise when the updated deviation index is a negative value, the product of tube current and exposure time is increased. Thereafter, the flow proceeds back to the step S130, and S131~S135 for determining whether the threshold condition is matched or not by the use of the corresponding updated deviation index.

At step S1355, the tube voltage is adjusted when the updated deviation index from the adjusted the product of tube current and exposure time is not ranged between the high threshold $\delta_{high}$ and the low threshold $\delta_{low}$. In another word, when the adjustment to the product of tube current and exposure time within a specific range can not enable the corresponding updated deviation index to fall in the ranged defined between the high threshold $\delta_{high}$ and the low threshold $\delta_{low}$, the flow will proceed back to the step S131 when the tube voltage is adjusted instead of the product of tube current and exposure time. Similarly, the tube voltage is decreased when the updated deviation index is a positive value, otherwise when the updated deviation index is a negative value, the tube voltage is increased. Thereafter, the flow proceeds back to the step S130, and S131~S135 for determining whether the threshold condition is matched or not by the use of the corresponding updated deviation index.

At step S1357, the evaluation process is stopped when the adjustment to the tube voltage within a specific range can not enable the corresponding updated deviation index to fall in the ranged defined between the high threshold $\delta_{high}$ and the low threshold $\delta_{low}$. Consequently, the tube voltage and the product of tube current and exposure time are determined and inputted by operator according to his/her experience.

After the tube voltage and the product of tube current and exposure time are determined and obtained from the aforesaid steps, the flow proceeds back to the step S140 of FIG. 4 for enabling an X-ray to be generated and projected on the target object 20 according to the corresponding imaging exposure parameters.

As shown in FIG. 3, the processor 130 provides and transmits the imaging exposure parameters to the X-ray source and the controller thereof 110 for generating an X-ray to the target object 20, and then to be detected by the digital X-ray imaging device 120.

Figure 9:
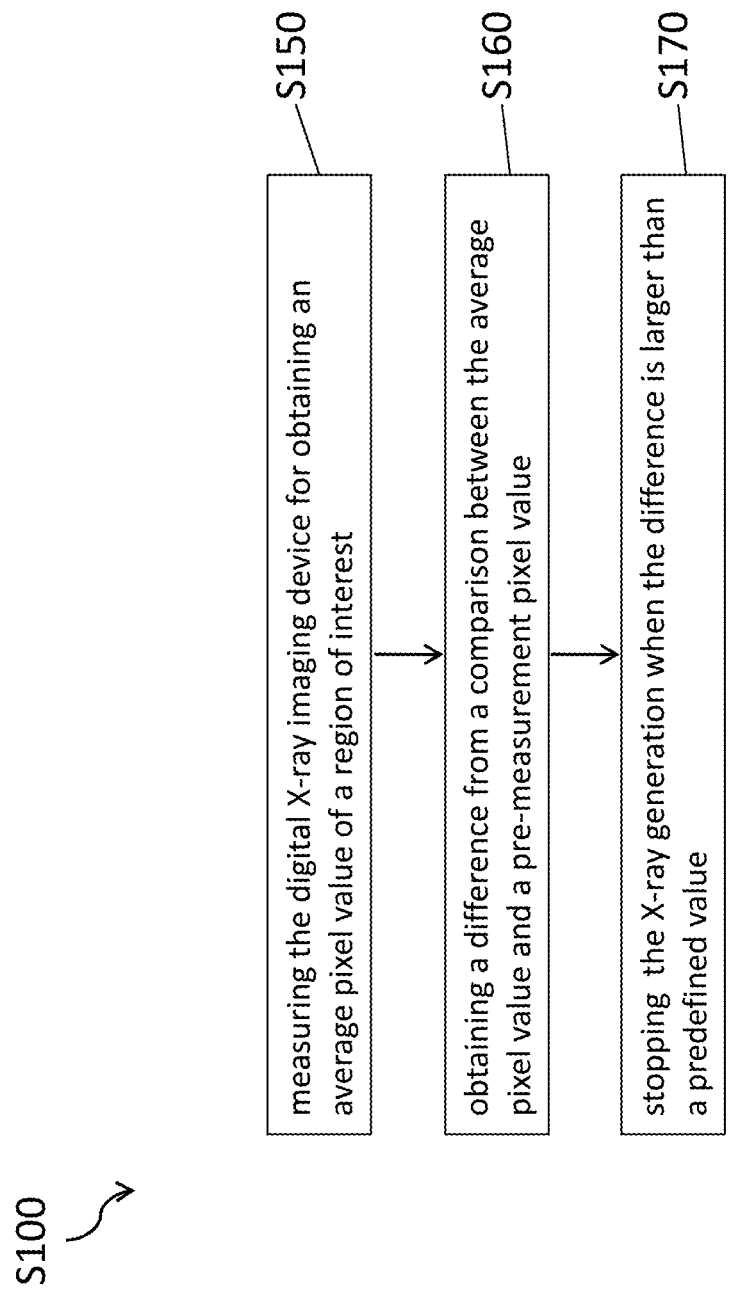
FIG. 9 is a flow chart depicting steps performed after the X-ray is being projected to the target object in the flow chart of FIG. 4.

For ensuring the imaging that is enabled at the step S140 to be a safe procedure and the imaging exposure parameters are limited within a safe range, the automatic exposure control method of the present invention further comprises the steps shown in FIG. 9. FIG. 9 is a flow chart depicting steps performed after the X-ray is being projected to the target object in the flow chart of FIG. 4.

The flow starts at the step S150. At step S150, the digital X-ray imaging device 120 is used to obtain an average pixel value $P_{meas}$ of a region of interest.

At step S160, a difference is obtained from a comparison between the average pixel value $P_{meas}$ and an average pre-measurement pixel value $P_{REF}$. It is noted that the $P_{REF}$ is substantially the average of all the pre-measurement pixel values pre-measurement pixel values Im in the ROI.

At step S170, the generation and projection of the X-ray is stopped when the difference is larger than a predefined value, by that the ensuring the imaging exposure parameters to be limited within a safe range.

To sum up, the aforesaid automatic exposure control system and method are adapted for a digital X-ray imaging device, and are being designed to use a depth sensor to detect the thickness of a region of interest (e.g. chest) of a target object (e.g. human body) so as to obtain a depth information accordingly, and then imaging exposure parameters can be estimated and obtained by comparing the depth information with a pre-established parameter database. Thereby, an X-ray imaging process can be performed according to the imaging exposure parameters for projecting an X-ray to the target object so as to be detected by the digital X-ray imaging device.

In addition, the aforesaid automatic exposure control system and method can be performed without the help of an additional single-channel or multi-channel AEC units, and thus, operators are able to select any position on a target object as region of interest without any consideration relating to where the AEC channels, or the availability and amount of ACE channels.

Moreover, as the aforesaid automatic exposure control system and method can be performed without the need of any pre-scan process, patients will not be subjected to overdosed radiation while at the same time an optimized personal X-ray imaging parameter advice can be provided to the patient, and thereby, not only the patient can have a low-radiation high-quality X-ray imaging, but also the risk of cancer can be reduced.

Furthermore, the imaging of the present invention is monitored in real time for obtaining an average pixel value $P_{meas}$ while a difference is obtained from a comparison between the average pixel value $P_{meas}$ and an average pre-measurement pixel value $P_{REF}$, by that the generation and projection of the X ray is stopped when the difference is larger than a predefined value, and therefore the imaging exposure parameters can be ensured to be limited within a safe range.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

What is claimed is:

1. An automatic exposure control system for digital X-ray imaging device, being adapted for imaging a target object, and comprising:
    an X-ray source,
    an X-ray source controller, for controlling a tube voltage and a product of tube current and exposure time of the X-ray source;
    a digital X-ray imaging device;
    a depth sensor; and
    a processor, embedded with a parameter database and connected to the X-ray source controller, the digital imaging device, and the depth sensor;
    wherein, the depth sensor is used for detecting a region of interest of a target object so as to obtain a depth information to be transmitted to the processor, and after receiving the depth information, the processor is enabled perform an estimation process according to the depth information and the parameter database so as to obtain an imaging exposure parameter for the X-ray source controller, and after receiving the imaging exposure parameter, the X-ray source controller is enabled to generate an X-ray accordingly so as to be projected onto the target object, and then to be detected by the digital X-ray imaging device;
    wherein the parameter database includes: at least one air-scan pixel value, at least one exposure index of air kerma, at least one equivalent thickness relating to the region of interest of a reference object, at least one X-ray attenuation coefficient, at least one exposure index relating to the region of interest of the reference object, and at least one pixel value of the digital X-ray imaging device; and
    wherein each air-scan pixel value is linear proportional to each exposure index of air kerma, while each exposure index relating to the region of interest of the reference object is linear proportional to each pixel value of the digital X-ray imaging device.

2. The automatic exposure control system of claim 1, wherein the depth sensor is a device selected from the group consisting of: a depth camera, a laser distance sensor, and an ultrasonic distance sensor.

3. The automatic exposure control system of claim 1, wherein the depth information is substantially an equivalent thickness relating to the region of interest of the target object that is obtained from the detection of the depth sensor.

4. An automatic exposure control method for digital X-ray imaging device, being adapted for imaging a target object, and comprising the steps of:
providing a parameter database, comprising the steps of:
establishing a first parameter lookup table and a second parameter lookup table, while enabling the first parameter lookup table to include at least one air-scan pixel value, at least one exposure index of air kerma as each air-scan pixel value is linear proportional to each exposure index of air kerma; and enabling the second parameter lookup table to include at least one equivalent thickness relating to the region of interest of a reference object; and
establishing a third parameter lookup table, while enabling the third parameter lookup table to include at least one exposure index relating to the region of interest of the reference object, and at least one pixel value of the digital X-ray imaging device, as each exposure index relating to the region of interest of the reference object is linear proportional to each pixel value of the digital X-ray imaging device;
using a depth sensor to detect the thickness of a region of interest of a target object for obtaining a depth information;
performing an estimation process for obtaining a set of imaging exposure parameters according to the depth information and the parameter database; and
generating and projecting an X-ray to the target object so as to be detected by a digital X-ray imaging device.

5. The automatic exposure control method of claim 4, wherein the using of the depth sensor to detect the thickness of a region of interest of a target object for obtaining a depth information further comprising the steps of:
providing an initial tube voltage and an initial product of tube current and exposure time for obtaining a corresponding air-scan pixel value and exposure index of air kerma from the first parameter lookup table;
performing a calculation to obtain a pre-measurement pixel value based upon the air-scan pixel value, the X-ray attenuation coefficient of a selected reference object, the equivalent thickness relating to the region of interest of the target object, and the equivalent thickness relating to the region of interest of the reference object;
calculating an exposure index relating to the region of interest of the target object basing upon the exposure index of air kerma, the pre-measurement pixel value and the air-scan pixel value;
performing an evaluation process by the use of an deviation index for determining whether or not a threshold condition is matched, while allowing the deviation index to be obtained basing upon the difference or ratio between exposure index relating to the region of interest of the target object and the corresponding exposure index relating to the region of interest of the reference object; and
forming the set of imaging exposure parameters of tube voltage and the product of tube current and exposure time when the deviation index conforms to the threshold condition.

6. The automatic exposure control method of claim 5, wherein the evaluation process for determining whether or not a threshold condition is matched by the use of the deviation index further comprises the steps of:
confirming that the threshold condition is matched when the deviation index is ranged between a high threshold and a low threshold;
adjusting the product of tube current and exposure time for updating the deviation index accordingly to be used in another evaluation process for determining whether a threshold condition is matched or not when the deviation index is not ranged between the high threshold and the low threshold;
adjusting the tube voltage when the updated deviation index from the adjusted the product of tube current and exposure time is not ranged between the high threshold and the low threshold; and
stopping the evaluation process for determining whether or not a threshold condition is matched when the deviation index from the adjusted tube voltage is not ranged between the high threshold and the low threshold.

7. The automatic exposure control method of claim 6, wherein the adjusting of the product of tube current and exposure time when the deviation index is not ranged between the high threshold and the low threshold further comprises the steps of:
lowering the product of tube current and exposure time when the deviation index is positive; and
raising the product of tube current and exposure time when the deviation index is negative.

8. The automatic exposure control method of claim 4, further comprising the following steps that are performed after the X ray are being projected to the target object:
measuring the digital X-ray imaging device for obtaining an average pixel value of a region of interest;
obtaining a difference from a comparison between the average pixel value and a pre-measurement pixel value; and
stopping the generation and projection of the X-ray when the difference is larger than a predefined value.

* * * * *